(12) United States Patent
Lalljee et al.

(10) Patent No.: US 10,232,359 B2
(45) Date of Patent: Mar. 19, 2019

(54) ABBREVIATED PROCESS TO CUSTOM-MAKE TITANIUM SILICATE BASED CATALYSTS WITH VARIEGATED PHYSICO-CHEMICAL PROPERTIES

(71) Applicant: SUD-CHEMIE INDIA PVT LTD, Kerala (IN)

(72) Inventors: Arshia Altaf Lalljee, Gujarat (IN); Rikeshchandra Sharadchandra Joshi, Gujarat (IN); Rajeshkumar Manubhai Patel, Gujarat (IN); Dhananjay Prabhakar Sabde, Gujarat (IN)

(73) Assignee: SÜD-CHEMIE INDIA PVT LTD., Kochi (IN)

( * ) Notice: Subject to any disclaimer, the term of this patent is extended or adjusted under 35 U.S.C. 154(b) by 0 days.

(21) Appl. No.: 14/915,297

(22) PCT Filed: Mar. 25, 2014

(86) PCT No.: PCT/IN2014/000189
§ 371 (c)(1),
(2) Date: Feb. 29, 2016

(87) PCT Pub. No.: WO2015/029055
PCT Pub. Date: Mar. 5, 2015

(65) Prior Publication Data
US 2016/0207033 A1    Jul. 21, 2016

(30) Foreign Application Priority Data
Aug. 30, 2013 (IN) .......................... 3890/CHE/2013

(51) Int. Cl.
*B01J 21/00* (2006.01)
*B01J 29/89* (2006.01)
*B01J 37/00* (2006.01)
*B01J 35/00* (2006.01)
*B01J 35/10* (2006.01)
*B01J 37/08* (2006.01)
*C07D 301/12* (2006.01)
*C07D 301/03* (2006.01)

(52) U.S. Cl.
CPC ............. *B01J 29/89* (2013.01); *B01J 35/002* (2013.01); *B01J 35/1033* (2013.01); *B01J 37/0009* (2013.01); *B01J 37/0018* (2013.01); *B01J 37/0063* (2013.01); *B01J 37/08* (2013.01); *C07D 301/12* (2013.01); *B01J 35/0026* (2013.01); *B01J 2229/40* (2013.01); *B01J 2229/42* (2013.01)

(58) Field of Classification Search
CPC .. B01J 35/002; B01J 2229/40; B01J 2229/42; B01J 29/89; B01J 37/0018; B01J 37/0026
USPC .......................................... 549/523; 502/242
See application file for complete search history.

(56) References Cited

U.S. PATENT DOCUMENTS

| 6,106,803 A | 8/2000 | Hasenzahl et al. |
| 6,551,546 B1 | 4/2003 | Grosch et al. |
| 6,849,570 B2 | 2/2005 | Hasenzahl et al. |
| 2003/0078160 A1 | 4/2003 | Hasenzahl et al. |
| 2003/0130116 A1 | 7/2003 | Hasenzahl et al. |

FOREIGN PATENT DOCUMENTS

| DE | 19623611 | * 12/1997 |
| DE | 19623611 A1 | 12/1997 |
| EP | 0265018 A2 | 4/1988 |
| EP | 1071506 A1 | 1/2001 |
| EP | 1138386 A1 | 10/2001 |
| EP | 1232007 B1 | 3/2005 |
| WO | 2011064191 A1 | 6/2011 |

OTHER PUBLICATIONS

Sabde et al, Synthesis of titanium silicalite-1 using ethyl silicate-40: a new silica source for zeolite synthesis, Journal of Materials Chemistry, 2000, 10(6), p. 1365-1370 (Year: 2000).*
International Search Report for PCT/IN2014/000189 dated Jul. 24, 2014.

* cited by examiner

Primary Examiner — Taylor V Oh
(74) Attorney, Agent, or Firm — Brown & Michaels, PC

(57) ABSTRACT

An abbreviated, energy efficient and manipulative process and recipe using a novel binder-combination, to custom-make shaped TS-1 product wherein, their physico-chemical attributes can be engineered, variegated or optimized independent of one another, according to specific stipulations for diverse catalytic reactions that employ them.

22 Claims, No Drawings

ABBREVIATED PROCESS TO CUSTOM-MAKE TITANIUM SILICATE BASED CATALYSTS WITH VARIEGATED PHYSICO-CHEMICAL PROPERTIES

FIELD OF THE INVENTION

This invention relates to the field of forming or shaping of Titanium Silicalite (TS-1) catalysts, which are used in a wide range of oxidation and other reactions. More particularly, this invention relates to a forming/shaping process-recipe that is engineered to custom-make TS-1 based catalysts in the form of extrudates, pellets or tablets, so as to vary one or more of its physico-chemical attribute/s independently of other/s, aimed at meeting the specific requirements of diverse industrial processes employing Titanium Silicalite based catalysts.

BACKGROUND AND PROBLEMS WITH THE PRIOR ART

Titanium Silicalites are crystalline porous materials. They are made up of tetrahedrallycoordinated Silicon and Titanium atoms surrounded by four Oxygen atoms. Said tetrahedrons of Silicon and Titanium are link up to form rings through corner sharing of Oxygen atoms. Such rings further link up to form three-dimensional Titanium Silicalite structures. Said rings define the pores that give these materials their characteristic properties as molecular sieves, adsorbents and catalysts. The size, shape and other parameters of said rings and of the associated pores determine the selectivity, activity and other properties of the catalyst. As far as this specification is concerned, the term 'shaped' is intended to cover transformed TS-1 (From raw TS-1 powder) in the form of an extrudate, tablet/pellet product that may be further sized to a granulated product. Adoption of other methods of fabrication is within the scope of the invention.

In this specification, unless otherwise required by the context, the term 'Titanium Silicalite-1' or 'TS-1' or 'Ti-ZSM-5' or 'Ti-MFI' refers to the raw form which is obtained through any of the hydrothermal and other processes for making raw Titanium Silicalite-1 reported in the art. Said processes for raw Titanium Silicalite-1(TS-1) yield the TS-1 in a lump or powder form. The material-in-process at the different steps of a process for making shaped TS-1 product is also referred to as TS-1 material. The meaning appropriate to the context may be adopted. The product obtained after said shaping/forming operation is referred to herein as the 'shaped Titanium Silicalite-1 product' or in short as 'shaped TS-1 product' or 'TS-1 product' or "TS-1 catalyst" or "TS-1 extrudates" or "TS-1 tablets" or "TS-1 pellets". It is also referred to herein at some places as 'Shaped TS-1' or "formed TS-1' or "TS-1 catalyst" or 'formed Titanium Silicalite-1 product'.

Titanium Silicalite (TS-1) comprises Ti(IV) and is an oxidation catalyst that has wide application in the organic transformations. It is a heterogeneous catalyst that is used in numerous oxidation reactions. It has good activity, selectivity and stability. It is usually used in conjunction with other oxidizing agents, such as for example, hydrogen peroxide with which it works particularly well. Some of the major reaction types wherein TS-1 catalyst is used are:

1) Epoxidation of olefins; oxidation of Propylene to Propylene oxide/Glycols and corresponding ethers; Allyl chloride to Epichlorohydrin,
2) Hydroxylation of aromatics; hydroxylation of phenol to Catachol and Hydroquinone;
3) Oxidation of alcohols; Alcohols to corresponding aldehydes or ketones
4) Oxidation of hydrocarbons; Parafins to corresponding alcohols/ketones.
5) Ammoxidation of Cylohexanone to Cyclohexanoneoxime, etc., Since the reactants and reaction-conditions of diverse industrial processes employing TS-1 catalysts are different, each of these processes markedly warrants unique/specific physico-chemical attributes and dimensions of the shaped TS-1 catalyst, or particular combinations thereof. However, the available processes of manufacture and fabrication of TS-1 products in the art adopt a one-size-fits-all-approach whereby the physico-chemical attributes and dimensions of the TS-1 product so manufactured are stereotypically restricted to a rather narrow range of combination-attributes. This is especially due to the lack of versatile recipes and/or process-engineering techniques in the art to tailor-make or optimize the attributes of the end product to suit the requirements of a given industrial process. The obvious result of this lacuna is a direct compromise on quality as well as resource economics of the industrial processes employing TS-1 catalysts. This is because the effective reaction rate depends not only on the temperature and the concentration of the reactants, but also on macrokinetic parameters such as phase boundary, bulk density, particle size of the catalyst, pore structure and the transport rate in the diffusion boundary layer. If the physical reaction steps are rate determining, then the catalyst capacity is not fully exploited due to an unsuited or incompatible physical configuration of the catalyst. The nature of crushing strength, bulk density and pore volume distribution and Ti availability, which are more concerned with the subject matter of this invention are explained as follows:

Crushing Strength:

Solid catalysts are usually dispatched in drums. During transport, storage and loading there is risk of damage to the catalyst from mechanical means. Even when the catalyst is placed in a fixed-bed reactor, the catalysts in each layer have to carry the weight of the catalysts in the above-lying layers. The catalyst should be able to resist the mechanical or other such stress. Hence crushing strength is measured to meet the requirement from end-user for a particular process. Crushing Strength (sometimes also referred to as "side crush strength") in general is measured by first placing a single piece of catalyst horizontally between two parallel plates or blocks and thereafter loading the assembly so that the piece is compressed and finally broken. A measure of the load required for cracking or breaking of a particle/unit is the crushing strength.

Bulk Density:

The bulk density of a catalyst is determined by measuring the volume of a known mass of catalyst sample. Whenever a process is scaled up to pilot or commercial scale, the form in which a catalyst is used is decisive for the ultimate performance of the unit. The catalyst thus will perform in a range of different physico-chemical properties (typically referred as catalyst specification). As far as bulk density is concerned, it is affected by the density of powder particles (used for forming/shaping) and the spatial arrangement of particles in the formed catalyst. Hence for guaranteed performance, a catalyst is supplied to the end-user with a range of bulk densities suitable in a particular process.

Pore Volume Distribution:

In general pore volume distribution can influence the reactions which are diffusion controlled. Pore volume distribution of the catalyst is one of the factors that influence the rate of the reaction.

The porous nature of the catalyst contributes substantially to the active surface area at which the catalytic reaction takes place. For the internal surfaces of the catalyst body (extrudates tablets/pellets) to be utilized effectively, the feed (reactants) must diffuse through the pores to reach the internal surfaces, and the reaction products must diffuse away from those surfaces and out of the catalyst body. The resistance to internal diffusion in the catalyst bodies can become a rate limiting factor in the reaction. Hence to overcome resistance to internal surfaces, the pore structure/pore volume of the catalyst is modified accordingly.

Ti Availability:

Ti(IV) in the TS-1 powder is responsible for catalytic activity in a given application. In the forming/shaping process, the more the content of TS-1 powder in forming/shaping recipe, the more active sites are accessible/available for the reactants.

It follows therefore that an optimal ratio of TS-1 Binder component has to be reached in order to maximize Ti availability while simultaneously sustaining superior degrees of crushing strength, bulk density and pore volume. For example, the catalyst with 10% binder component will have more active sites than a catalyst with 20% binder component.

However, the optimal ratio of TS-1 and Binder may not be same for different applications. In general, if the application demands more Ti availability then the catalyst should contain either no binder or minimum binder to give the desired physico-chemical properties and performance. Owing to the requirement of specific applications, the Ti content in the catalyst needs to be fine-tuned to suit the applications. Besides, more Ti in catalyst may not always be necessary and/or desirable for all industrial applications. For example, more Ti in some oxidation applications leads to more exothermicity, which may result in decomposition of the oxidant. In such cases it is desirable to reduce the Ti content (i.e. Ti availability) to suit a particular application.

There has always been a gap between the configuration-demands of the industry and the state of the art-supply of TS-1 (specifications/attributes) due to the said one-size-fits-all-approach in the state of the art. For example the requirement for bulk density and crushing strength for epoxidation of propylene to propylene oxide may not be the same as required for epoxidation of Allyl chloride to Epichlorohydrin. There is therefore an urgent and long-felt need for process-engineering techniques that can custom-make or at least simultaneously vary or optimize a plurality of attributes of the shaped TS-1 product to suit the requirements of diverse industrial processes that employ Titanium based catalysts.

Yet another problem faced especially by manufacturers of shaped TS-1 product is the inflexibility and inadaptability of the prevalent process recipes in the art, owing to especially (a) the tedium of the long-drawn-out, energy intensive mechanical, physical and chemical process steps that have evolved thus far in the art, and also (b) the narrow range of alternatives to choose from as regards the ingredients that go into transformation of raw TS-1 to the shaped TS-1 extrudates, tablets/pellets or granules.

In the process for forming the TS-1 extrudate (also referred to as formed TS-1) disclosed in U.S. Pat. No. 6,551,546, Tetra Ethyl Ortho Silicate is hydrolyzed, and the ethanol generated by hydrolysis is removed by distillation to obtain silica sol. The sol is used as binder along with TS-1 for making microspheres (by Spray drying). The raw TS-1 material is in the form of a spray dried powder is mixed with the proprietary binder Ludox AS-40 (DuPont, now Grace) which is a colloidal silica binder. Methylcellulose and water are also added to convert the TS-1 composite into a paste. Optionally fumed silica/PEG (polyethylene glycol) are also added, and TS-1 is densified prior to shaping.

In U.S. Pat. No. 6,849,570, the binders used either contain Al or Na or other cationic impurities, which are not desirable for oxidation reactions performed using hydrogen peroxide as oxidant, since the presence of Al or Na or other trace metal impurities is detrimental as it accelerates the decomposition of hydrogen peroxide, thereby resulting in either poor efficiency and/or inferior performance.

In the process disclosed in US application 20030130116, Methyl cellulose and Alumina are added to spray dried raw TS-1 powder. Requisite amount of water is incorporated to obtain a paste which is kneaded. Partially hydrolyzed Tetra Ethyl Ortho Silicate (Ester 40 from Wacker, 40% SiO2) is used as binder. The ethanol generated by hydrolysis is removed from the reaction mixture since 40 wt % silica binder can only be produced from Tetra Ethyl Ortho Silicate when the ethanol is evaporated.

In the process disclosed in EP1071506B1 and U.S. Pat. No. 6,551,546 B1, Tetra Ethyl Ortho silicate is hydrolyzed, and ethanol generated by hydrolysis is removed by distillation to obtain silica sol. This sol is used as binder with TS-1 to form a spray dried material. The spray dried material is further shaped using binders such as Silica Sol, Ludox AS-40.

In U.S. Pat. No. 6,106,803, the process for preparing Titanium Silicalite-1 granulates comprises, hydrolyzing TEOS with alkyl ammonium hydroxide. Subsequently mixing with TS-1 powder and spray drying to obtain Titanium Silicalite-1 microgranules.

Prior art thus reveals long-drawn-out processes which are not only time consuming but also resource intensive and cost prohibitive due to the following disadvantages, among others;

(a) US 20030130116 A1, EP1071506B1, U.S. Pat. No. 6,551,546 B1, among others, use Tetra Ethyl Ortho silicate (TEOS) as binder precursor which is expensive.

(b) Further, when the Tetra Ethyl Ortho silicate is hydrolyzed, ethanol generated by hydrolysis needs to be removed. This is a time consuming and resource intensive step that substantially increases process cost.

(c) Other commonly used binders and forming aids used in prior art include, silica precursors such as Ludox AS-40, Silica sol, Tetra-n-propylammonium hydroxide, etc., wherein the Na content and other metal impurities are high.

(d) Spray drying (prior to forming, extrusion etc.,) is an integral step in prior art processes which is not only time consuming but also resource intensive and thereby increases process costs.

(e) A further problem faced by manufacturers of shaped TS-1 product is the constraints imposed by certain process steps employed in the making of shaped TS-1 using raw TS-1 powder which inflict a restrictive influence on the versatility of the TS-1 product so manufactured. For example, as also documented in prior art literature [including US 20030130116 A1], extrusion to turn out shaped TS-1 product is not possible with calcined Titanium silicate, which has proved to be a major stumbling block where TS-1 extrudtaes are required to be manufactured. This is again due to the shortcomings in the process-recipes in vogue which impose this, among other, restrictions. In case of the process used especially by US 20030130116, the calcined TS-1 already contains silica sol which is added prior to spray drying the TS-1. Hence the desired rheology is not achieved in the paste, which may be responsible for not achieving extrution with calcined TS-1.

There is therefore an urgent and long-felt need for a versatile recipe and a process that ensures economics of both time and resources, and also provides for custom-making or at least varying/optimizing the combination-attributes of shaped TS-1 product to match the requirements of diverse industrial processes that employ Titanium based catalysts.

These inventors have, after extensive research, devised (a) an abbreviated (shortened) process recipe (b) comprising a novel binder composition (c) which lends surprising versatility to the process wherein, the said process can be manipulated to custom-make shaped TS-1 extrudates, tablets or pellets, whereby their physico-chemical attributes such as but not limited to crushing strength, bulk density, Ti availability and prore volume distribution etc., can be individually engineered to suit specific requirements of diverse industrial processes employing Titanium based catalysts.

To overcome the disadvantages of prior art processes, alternate recipes comprising exotic binder compositions were explored by these inventors who hypothesized that in order to custom-make TS-1 product with different physico-chemical attributes, a unique binder or binder-combination thereof, with a superior silica yield and binding potential was vital. After several trials of varied combinations including with common binders used in the art had failed, Oligomeric silicates were tested. Oligomeric silicates are condensed, transparent liquids containing varying amount of $SiO_2$ wt % ($SiO_2$ content after hydrolysis). Of this group, Ethyl Silicate 40 [ETS-40 hereinafter] was chosen especially owing to its potential to yield higher silica (40 wt %) and being more economical than TEOS. Thereafter, adding a manipulative dimension to the recipe was explored with a view to provide for engineering the physico-chemical attributes of the shaped TS-1 product. During the course of testing several hypotheses to variegate one attribute of TS-1 with respect to others, a serendipitous find was encountered by these inventors wherein, it was concluded after several subsequent confirmatory tests that upon partial hydrolyses of ETS-40 the resultant 'ethanol in combination with remaining ETS-40' proved to be surprisingly and substantially superior to prior art binder precursors. It is pertinent to mention that 'ETS-40-Silica-Ethanol-water-ammonia combination' has never been used in the art as a binder precursor. This aspect is both novel and inventive as against the commonly accepted norm in prior art wherein ethanol generated by hydrolysis of TEOS had a counterproductive effect on the TS-1 forming process and therefore in all prior art processes the ethanol so generated had to be necessarily removed/drained out, before proceeding with the subsequent process steps of extrusion, tableting/pelleting etc., This prior art process step of removal of ethanol is not only time consuming but also has substantial cost implications. For making one Kg of TS-1 extrudates, 500 g of ETS-40 is used and up to 300 g of Ethanol is generated during hydrolysis in the present process, whereas in prior art process 715 g of Tetra ethyl ortho silicate (TEOS) is used and ~540 g of Ethanol is generated. Due to multiple steps (such as spray drying, ethanol removal etc) involved in the prior art process, the processing costs are high compared to the present process. The cost of TEOS is approximately ~1.5 times higher than ETS-40. Hence the present process is cost effective as both the raw material cost, processing cost are comparatively lower than prior art process. Removal of Ethanol is an additional step in the prior art processes, which is not only time consuming but also energy intensive.

Further interesting aspects about retention of Ethanol formed after the hydrolysis of ETS-40 during forming/shaping and its effect on the physico-chemical attributes of the shaped TS-1 were also studied. A number of experiments were carried out to regulate and re-regulate the hydrolysis stage-wise by administering varied amounts of ammonia into the reaction mixture/recipe and optionally secernating the said hydrolysis step. The hydrolysis conditions such as quantity of ammonia added and hydrolysis time significantly affect the resultant product properties, It was observed that hydrolysis conditions influenced the properties in the shaped product. Yet another novel observation of this invention is that a slow progression of the hydrolysis reaction results in a superior product and also provides means to regulate the properties of the final shaped TS-1 product.

Thus, controlling the hydrolysis process and content of unique binder precursor of this invention provides for control over the final product properties such as Crushing strength (CS), Bulk density (BD) and pore volume distribution and Ti availability in the final product. In the case of ETS-40-Silica-Ethanol-ammonia-water binder recipe of this invention, the hydrolysis reaction is spilled over beyond the said shaping operation. By extending said hydrolysis process and by controlling the duration thereof it was found that the final physico-chemical parameters of the shaped TS-1 product can be engineered. This invention finds that the duration of hydrolysis, amount of ammonia added, amount of water added and drying time etc., influence the final product properties which have been illustrated in tables below a particular set of examples.

Thus, experiments with this novel recipe categorically indicated to provide for said engineering of physico-chemical attributes of shaped TS-1. Towards this objective, the present invention involves a drying step at elevated temperature such that by adjusting the drying time, said final physicochemical properties can be fine tuned and optimized to obtain the desired the crushing strength and other properties. This is novel and inventive over prior art processes.

These inventors went on to establish that the extrudate (and the granulated product) properties are influenced by the following, among other, factors:

(i) The amount of aq. $NH_3$, the hydrolysing agent that is added;
(ii) The amount of water along with ammonia;
(iii) The amount of the unique binder precursor added
(iv) The duration of the operation of mixing of ETS-40 and dil. $NH_3$, that is, the stirring period and
(v) The drying time;

By regulating the above parameters, a surprising degree of control of the extrudate properties such as BD(Bulk Density), CS(Crushing strength) and Ti availability were observed by the invention, which is novel and inventive over prior art processes. The term 'extrudate properties' herein also includes the granulation, pelletized or tabletted product properties, unless otherwise required by the context. The shaping processes downstream of dough formation, namely, extrusion, tableting/pelleting and granulation are jointly referred to herein as fabrication processes or shaping process or forming process. Within the scope of the invention, the term fabrication includes all other feasible processes for handling/shaping of the dough material to obtain a discrete TS-1 catalyst product.

The binding action of ETS-40 is not adversely affected by presence of ethanol. As would be observed, ethanol is generated with the progress of the hydrolysis of ETS-40. Although prior art processes specifically eliminated ethanol in their respective processes, these inventors found that the presence of ethanol in the dough did not adversely affect the overall forming process. A higher ethanol concentration slows down the hydrolysis reaction and provides added scope for said manipulation/engineering of physico-chemical attributes of shaped TS-1. This is very advantageous because it does away with the necessity of removal of the generated ethanol, and/or other alcohols that is required when binders of the prior art are adopted. As mentioned, when the binder of this invention is adopted, the generated alcohol turns out to be a useful component of the TS-1 and binder mixture as the same creates the desired porosity in the product. Overall, removal of the alcohol by an energy-intensive operation is thus avoided.

References to the TS-1 and binder mixture herein are intended to include the forming compounds and/or other optional additives that may be added to form a part of the dough mixture.

OBJECTS OF THE INVENTION

The main object of this invention is therefore to provide a $_m$anipulative process and recipe for the custom-manufacture of shaped TS-1 (extrudates, tablets/pellets and other shapes) with an assortment of physico-chemical attributes that can be engineered or at least simultaneously variegated/optimized according to the stipulations for diverse catalytic reactions that employ them.

Another main object of this invention is to employ an advanced process-recipe to custom-make shaped TS-1 comprising a unique, hitherto unidentified and untested binder-composition which lends surprising versatility to the process and the products thereof.

Another main object of this invention is to control and regulate the process steps of, primarily but not limited to, hydrolysis during the transformation of raw TS-1 mixture, to obtain shaped TS-1 product with desired physico-chemical attributes including but not limited to curshing strength, bulk density, prore volume distribution and higher Ti availability etc., according to a given stipulation Another main objective of this invention is to provide for a manipulative process-recipe to custom-make shaped TS-1 (extrudates, pellets/tablets and other shapes), which is much simpler, quicker owing to fewer process steps (i.e., abbreviated), more energy efficient and is less resource intensive (economical) compared to other competing processes in the art.

A further object of this invention is to provide for a manipulative process-recipe to custom-make shaped TS-1 (extrudates, pellets/tablets and other shapes), which obviates the step of removing ethanol and also the step/s of spray drying.

Another object of this invention is to provide for a manipulative process-recipe to custom-make shaped TS-1 (extrudates, pellets/tablets and other shapes), wherein shaping of TS-1 product is possible with calcined as well as non-calcined TS-1 powder.

STATEMENT AND SUMMARY OF THE INVENTION

According to the invention therefore, there is provided an abridged, energy efficient and manipulative process-recipe to custom-make shaped TS-1 (extrudates, pellets, tablets) with an assortment of physico-chemical attributes that can be engineered or at least simultaneously variegated/optimized independent of one another, according to the stipulations for diverse catalytic reactions that employ them, comprising one or more of the following steps;

i) providing powdered raw Titanium Silicalite-1(TS-1) material which may or may not have undergone calcination;

ii) adding to the TS-1 material from step (i), a 'Binder composition' comprising a combination of one or more Oligomeric silicate and one or more alcohols, and at least one hydrolysing agent either in a pre-mixed condition or sequentially wherein, the said Oligomeric silicate is either partially or completely hydrolyzed depending upon the targeted physico-chemical characteristics of the shaped TS-1; and further wherein optionally the said hydrolysis can be secernated;

iii) forming the TS-1 material mixture from step (ii) into a dough;

iv) fabricating the dough from step (iii) into shaped TS-1 by means of an operation such as extrusion followed by cutting, or granulation followed by compacting, or other fabrication operation;

v) Drying and calcination of the shaped TS-1 material from step (iv) at elevated temperature for a pre-determined period of time;

wherein, the properties of the end product (extrudate) can be engineered or optimized by employing one or more of the following steps, or any combination thereof;

(a) The crushing strength and bulk density can be gradually increased with increase in the binder content.

(b) The crushing strength and bulk density can be gradually decreased with increasing water content.

(c) The crushing strength and bulk density can be gradually decreased with increasing the content of the hydrolyzing agent.

(d) The crushing strength and bulk density can be gradually decreased with increasing stirring time (during hydrolysis of the binder mixture).

(e) the crushing strength and bulk density can be gradually decreased with increasing drying time, and further wherein, the properties of the end product (Tablets and Pallets) can be engineered or optimized by employing one or more of the following steps, or any combination thereof;

(f) addition of starch to the said Binder composition in step (ii) hereabove—as such or either with water or with Ethyl silicate, to sustain a given value of crushing strength while varying the bulk density alone, which can be increased with decreasing the starch content, (g) addition of one or more blowing agent during mixing (making dough)—as such i.e not in combination with either Ethyl silicate or water, to drastically decrease the crushing strength alone.

(h) addition of one or more blowing agent along with ethyl silicate—during mixing (making dough)—to drastically increased the bulk density alone, and still further wherein, the availability of Titanium catalyst can be increased by lowering the binder-composition content, and/or by limiting hydrolysis during the hydrolysis stage whereby larger pore size is achieved; and optionally secernating the hydrolysis step to regulate pore volume distribution;

DETAILED DESCRIPTION OF THE INVENTION

It is pertinent to mention that although this specification makes reference to TS-1 in the description and the examples of the invention, the novel process recipe and methods for manipulation/engineering of the physico-chemical attributes to custom-make shaped TS-1, without limitation, extend to all (silica based) carriers for other catalysts as well. For the purposes of this specification, the term 'Binder composition' or 'binder' in the context of the instant invention means and includes the binder-combination comprising a mixture of (a) one or more Oligomeric silicate, (b) one or more alcohols and, (c) at least one hydrolysing agent either in a pre-mixed condition or sequentially, in addition to optionally (d) other additive/s, wherein, any combination thereof acts as a binder or increases binding strength of the end product.

As mentioned, this invention provides a process wherein powdered Titanium Silicalite-1 material is converted into a shaped Titanium Silicalite-1 product by the application of a novel binder. The dough obtained after the application of the binder(s) to the powdered raw TS-1 material is subjected to a fabrication operation to give the said shaped product. Said fabrication operation may be either an extrusion operation to give an extrudate product or a granulation operation followed by compaction to give a pellet or tablet product.

In the preferred process of the invention, the powdered raw TS-1 is taken and contacted with the Binder composition of the invention which is a combination of primarily, ethyl silicate, water, ammonia and Ethyl alcohol/ethanol. The said ethyl silicate (ETS-40) contains about 40% by wt of silica. ETS 40 is taken and a hydrolysing agent is added. This initiates the hydrolysis. Ethanol is generated as a result of the said hydrolysis which forms the said Binder composition.

The hydrolysis is allowed to proceed till a pre-determined stage i.e typically hydrolysis of ETS-40 from 10 to 90% level and at that stage the binder-hydrolysis agent mixture is added to the raw TS-1 material. Said addition is carried out over a predetermined period of time. This is the preferred arrangement of the invention. Within the scope of the invention, the binder-hydrolysis agent mixture may be partly or fully hydrolyzed at the time of the addition thereof to the raw TS-1 powder.

Therefore the terms 'binder', and 'binder composition' used in the description of the embodiments and examples of this invention, unless incoherent with the context, shall mean a combination of ETS-40, silica, Ethanol, water, ammonia with or without other additives. One of the objectives of the process of the invention is to extend the said hydrolysis process and to let it spill over beyond the said initial operation(s) wherein the raw TS-1 material, ETS-40, the hydrolysing agent and the optional ethanol are brought together and the dough formed. Said initial operations broadly comprises mixing of the components which may be carried out in any suitable mixing equipment. Different arrangements are possible for the bringing together of the TS-1 mixture components and are all within the scope of the invention. Preferably, an Eirichmixer or a mix muller is used. Said initial operations may also comprise optionally kneading, homogenising, densification and other operations.

One aspect of the control of the formation of the TS-1 product of the invention is by regulating the degree of hydrolysis of the binder precursor i.e stirring/hydrolysis time before the addition thereof to the raw TS-1 material and by regulating the addition of the binder-hydrolyzing agent mixture to the TS-1 material.

As mentioned, the shaped TS-1 product characteristics such as BD, CS, pore volume distribution and Ti availability, can be influenced by varying the parameters of the hydrolysis process of the ETS-40-ethanol binder, in particular by changing the duration of the process in the pre-dough and post-dough stages. Higher degree of hydrolysis prior to the adding of the ETS-40, aq. NH3, and ethanol mixture to the TS-1 and HPMC mixture tends to reduce CS and BD of the final extrudate product. Extending said ETS-40 hydrolysis into the curing and drying stages tends to alter the CS, pore volume distribution and the BD.

The degree of said hydrolysis can be controlled by the quantity of the hydrolysingagent(aq. ammonia) added and the stirring time allowed for hydrolysis before the said addition of the ETS-40 mixture to the said powder mixture. It may be noted that the progress of the hydrolysis reaction affects the subsequent condensation reactions; the greater the extent of the hydrolysis the greater will be the polymerization (condensation) of the silica species i.e more of Q3 and Q4 silica species are formed.

The amount of the binder and the amount of the hydrolyzing agent used have an effect on the properties of the final TS-1 shaped product. Water comes into the reacting system through the application of the binder as an aqueous solution and also the application of the hydrolysis agent such as when aqueous ammonia is adopted as the hydrolysing agent. Also, water may be required to be added to adjust the dough consistency.

The effect of binder and the amount of the hydrolyzing agent on product properties depend on whether the process adopted for said shaped TS-1 product is the extrusion route, or the granulation route or tableting/pelleting route.

Said Effects in the Case of the Extrusion Route are as Follows;

In the experiment of the invention employing the said extrusion route the dough was extruded with 3 mm diameter size.

Where the binder solution is added first to the TS-1 material, the control is achieved by the regulation of the rate of addition of the hydrolyzing agent to the binder-TS-1 mixture. A pre-determined degree of hydrolysis, that is, a pre-determined progress of the said hydrolysis is planned to be achieved by the time of the completion of the said initial operations, that is, up to dough formation. The remainder of the hydrolysis reaction is then required to be completed in the post shaping stages. To achieve good control over this part of the said hydrolysis process, this invention provides for a stage of curing/drying operation. Duration of the curing stage, properties can be carefully controlled so as to achieve the desired physicochemical properties in the final shaped TS-1 product. The term "post-addition" stage shall also be understood to mean post-shaping operation stage.

This invention has found that providing for a greater degree of said hydrolysis in the post-addition stages, that is, in the said curing stage results in enhanced crushing strength (CS) of the shaped TS-1 product. CS and BD (Bulk Density) of the product were found to increase with increasing binder content. The binder amount remaining the same, administering thereof to the raw TS-1 powder in the form of a more dilute aqueous solution i.e more water content, results in decrease in CS and BD.

The amount of the hydrolyzing agent, which is ammonia in the preferred embodiment, was found to affect the CS and BD both of which were found to decrease with increasing ammonia content.

The Effects When the Granulation Route is Adopted are Found to be as Follows:

In this investigation, the dough was subjected to drying and granulation. The granulated material was then compacted into tablets/pellets of 3 mm dia. size.

No significant effect was observed on the shaped TS-1 product properties upon variation of the amount ammonia, the hydrolysing agent added to the raw powdered TS-1.

In this investigation wherein said tablets were produced, starch was added to the dough mixture as a blowing agent so as to obtain a lighter and more porous shaped-TS-1 product having a lower BD. Addition of starch as blowing agent or extrusion aid affected the CS and BD significantly. The effect of starch addition to the dough was further investigated as follows; two methods of starch addition were studied. In one method starch was added to the dough mixture together with water. In another experiment, the starch was added as such and not in combination with any other component.

Addition of starch by itself caused a sharp drop in BD. BD was found to decrease with increasing starch quantity. It was observed that the CS achieved was highest when the starch addition was done together with water, all other factors such as the starch quantity remaining the same. Addition of the starch directly had a very strong effect on the BD leading to a substantial decrease in BD.

Within the scope of the invention, other additives may be added to the TS-1 and binder mixture. Such additives may include forming additives, viscosity-enhancing additives, additives for increasing the stability/activity of final product.

Preferably, HPMC(Hydroxyl propyl methyl cellulose) is added to the TS-1. The binder composition is added to convert the mixture into dough (paste). A kneading operation is not necessary in the shaped TS-1 process of the invention but can be optionally adopted if desired. Said paste is homogenized in a mixing operation preferably carried out in an Eirich mixer or a Mix Muller. Additional operations such as mixing, homogenizing, densification, kneading may be incorporated optionally if found necessary/useful.

The dough is then extruded using a suitable extruder. Any of the known extruders in the art may be used. Preferably, a Ram extruder or a screw (single, double) or piston type extruder is used. The extruded material is cut into pieces of desired length. The cutting operation may be carried out on the extruder by suitable adjustment of the knife or die cutter or other such cutting devices. Alternatively, other cutting means may be adopted. Said cutting may also be carried out as a separate operation.

Said catalyst pieces are dried by any of the known procedures for drying using any of the known equipment. The dried pieces are then calcined. During calcining the HPMC and ammonia are substantially eliminated. The product is shaped TS-1 product and contains silica that comes from the added ETS-40.

Drying time has considerable influence on the extrudate characteristics. During the drying of the green extrudates, further hydrolysis and subsequent polymerization of silica is affected resulting in binding with TS-1 particles. The water required for the progress of the hydrolysing reaction during these stages comes from the green extrudate material. If hydrolysis time is reduced a large-pore extrudate is obtained, the CS value remaining substantially the same.

In order to provide a clearer understanding of the invention and without any limitation to the scope of the invention, a few of the embodiments thereof are described hereinbelow as examples to show variegated attributes of TS-1 product.

EXAMPLES

Preparation of TS-1 Based Extrudates

Preparation of Extrudates with BD in the Range of 0.58 to 0.62 kgs/lit.and CS in the Range of 4 to 7.5 Kgs:

Example 1

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 0.5 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 6 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 1.

Example 2

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 3 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 1.

container. To this was added 200 ml DM water and 3 ml of 14 N liquor ammonia. This solution was stirred for 3 hr. 1 Kg TS-1 powder was mixed with 20 g of HPMC in an Eirich

TABLE 1

Properties of TS-1 based extrudates with BD in the range of 0.58 to 0.62 kgs/lit and CS in the range of 4 to 7.5 Kgs:

| Ex No. | TS-1 Powder wt % in final catalyst (wt %) | Binder composition content (SiO2 wt %) | Ethyl silicate hydrolysis conditions | | | | | Ave. | |
|---|---|---|---|---|---|---|---|---|---|
| | | | DM water (ml) | Liq. Ammonia (ml) | HPMC (g) | Stirring time (h) | drying time, (h) | Crushing strength (Kgs) | Bulk Density (Kg/lit) |
| 1 | 80 | 20 | 200 | 2 | 20 | 0.5 | 6 | 7.2 | 0.6 |
| 2 | 80 | 20 | 200 | 2 | 20 | 3 | 12 | 4 | 0.6 |

Preparation of Extrudates with BD in the Range of 0.57 to 0.65 kgs/lit.and CS in the Range of 3.5 to 4.5 Kgs:

Example 2

As described above. The properties of the same are tabulated in the Table 2.

Example 3

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 2.

Example 4

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 2.

TABLE 2

Properties of TS-1 based extrudates BD in the range of 0.57 to 0.65 kgs/lit. and CS in the range of 3.5 to 4.5 Kgs:

| Ex. No. | TS-1 Powder wt % in final catalyst (wt %) | Binder composition content (SiO2 wt %) | Ethyl silicate hydrolysis conditions | | | | | Ave. Crushing strength | Bulk Density (Kg/lit) |
|---|---|---|---|---|---|---|---|---|---|
| | | | DM water (ml) | Liq. Ammonia (ml) | HPMC (g) | Stirring time (h) | drying time, (h) | | |
| 3 | 80 | 20 | 200 | 2 | 20 | 1 | 12 | 4.5 | 0.62 |
| 2 | 80 | 20 | 200 | 2 | 20 | 3 | 12 | 4 | 0.6 |
| 4 | 80 | 20 | 200 | 3 | 20 | 3 | 12 | 3.85 | 0.57 |

Preparation of Extrudates with BD Greater Than 0.65 kgs/lit.and CS Greater Than 7.5 Kgs:

Example 5

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 0.5 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 3.

Example 6

For making binder solution for 1 Kg TS-1 powder, 1071 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from Eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 3.

TABLE 3

Properties of TS-1 based extrudates with BD greater than 0.65 kgs/lit. and CS greater than 7.5 Kgs:

| | TS-1 Powder wt % in | Binder composition | Ethyl silicate hydrolysis conditions | | | | Ave. | |
|---|---|---|---|---|---|---|---|---|
| Ex. No. | final catalyst (wt %) | content (SiO2 wt %) | DM water (ml) | Liq. Ammonia (ml) | HPMC (g) | Stirring time (h) | drying time, (h) | Crushing strength (Kgs) | Bulk Density (Kg/lit) |
| 5 | 80 | 20 | 200 | 2 | 20 | 0.5 | 12 | 12.8 | 0.66 |
| 6 | 70 | 30 | 200 | 2 | 20 | 1 | 12 | 12.5 | 0.67 |

Preparation of Extrudates with BD Lesser Than 0.58 kgs/lit. and CS Lesser Than 3.5 Kgs:

Example 7

For making binder solution for 1 Kg TS-1 powder, 625 g ethyl silicate 40 was taken in a 2 liter poly propylene container. To this was added 400 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 4.

Example 8

For making binder solution for 1 Kg TS-1 powder, 278 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. The same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 12 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 4.

TABLE 4

Properties of TS-1 based extrudates with BD lesser than 0.58 kgs/lit. and CS lesser than 3.5 Kgs:

| Sr No. | TS-1 Powder wt % in final catalyst (wt %) | Binder composition content (SiO2 wt %) | Ethyl silicate hydrolysis conditions | | | | | Ave. | |
|---|---|---|---|---|---|---|---|---|---|
| | | | DM water (ml) | Liq. Ammonia (ml) | HPMC (g) | Stirring time (h) | drying time, (h) | Crushing strength (Kgs) | Bulk Density (Kg/lit) |
| 7 | 80 | 20 | 400 | 2 | 20 | 1 | 12 | 3.5 | 0.58 |
| 8 | 90 | 10 | 200 | 2 | 20 | 1 | 12 | 2.7 | 0.54 |

Preparation of Extrudates Containing Ti Content in the Range of 1.4 wt % to 2.0 wt %

Refer Examples 3, 8 and 6 as described above. The said product from these examples was characterized for crushing strength and bulk density and Ti content. The properties of the same are tabulated in the Table 5.

TABLE 5

Properties of TS-1 based extrudates with varying Ti content/binder content. content

| Sr No. | TS-1 Powder wt % in final catalyst (wt %) | Binder composition content (SiO2 wt %) | Ethyl silicate hydrolysis conditions | | | | | Ave. | | |
|---|---|---|---|---|---|---|---|---|---|---|
| | | | DM water (ml) | Liq. Ammonia (ml) | HPMC (g) | Stirring time (h) | drying time, (h) | Ti content (wt %) | Crushing strength (Kgs) | Bulk Density (Kg/lit) |
| 3 | 80 | 20 | 200 | 2 | 20 | 1 | 12 | 1.82 | 4.5 | 0.62 |
| 8 | 90 | 10 | 200 | 2 | 20 | 1 | 12 | 1.96 | 2.7 | 0.54 |
| 6 | 70 | 30 | 200 | 2 | 20 | 1 | 12 | 1.48 | 12.5 | 0.67 |

Preparation of Extrudates with Varying Pores Size Distribution.

Examples 1

As described above. The properties of the same are tabulated in the Table 6

Example 9

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 4 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and the same was removed from eirich mixer and transferred to a single screw extruder fitted with a 3 mm multi hole die at the mouth piece. The dough was extruded to make 3 mm green extrudates. These green extrudates were allowed to age for 12 hours at room temperature in an open atmosphere. Post ageing, the green extrudates were dried at 120° C. in an air oven for 6 hours, followed by calcinations in air flow at 550° C. for 3 hrs at a heating rate of 1.5° C./minute. Calcined TS-1 extrudates constituted the shaped TS-1 product. The said product was characterized for crushing strength and bulk density. The properties of the same are tabulated in the Table 6.

TABLE 6

Properties of TS-1 based extrudates with different prore volume distribution.

| Ex No. | TS-1 Powder wt % in final catalyst (wt %) | Binder composition content (SiO2 wt %) | Ethyl silicate hydrolysis conditions | | | | | Ave. | | | Meso and macro- pore volume (%) |
|---|---|---|---|---|---|---|---|---|---|---|---|
| | | | DM water (ml) | Liq. Ammonia (ml) | HPMC (g) | Stirring time (h) | drying time, (h) | Crushing strength (Kgs) | Bulk Density (Kg/lit) | Micropore volume (%) | |
| 1 | 80 | 20 | 200 | 2 | 20 | 0.5 | 6 | 7.2 | 0.6 | 78 | 22 |
| 9 | 80 | 20 | 200 | 2 | 20 | 4 | 6 | 6.3 | 0.61 | 97 | 3 |

Preparation OF TS-1 Based Tablets/Pellets

Preparation of Pellets/Tablets with BD in the range of 0.62 to 0.69 kgs/lit.and CS in the Range of 3.6 to 6.8 Kgs:

Example 10

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and mixed further for 30 minutes. Dough was transferred to an air oven and dried at 120° C. for 12 hours. Post drying, the lumps obtained were pressed through a granulater of 1 mm dia (BSS 16 mesh) to make feed granules. This feed was then transferred to a tableting machine where in the feed was converted to tablets having both dia and length 3 mm. These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 7.

Example 11

For making binder solution for 1 Kg TS-1 powder, 625 g ethyl silicate 40 was taken in a 2 liter poly propylene container. To this was added 200 ml DM water and 3 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. A dough was obtained after 30 minutes and mixed further for 30 minutes. Dough was transferred to an air oven and dried at 120° C. for 12 hours. Post drying, the lumps obtained were pressed through a granulater of 1mm dia (BSS 16 mesh) to make feed granules. This feed was then transferred to a tableting machine where in the feed was converted to tablets having both dia and length 3 mm. These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 7.

Example 12

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr . 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. 100 g starch powder was mixed with 400 ml DM water, and added to the Eirich mixer containing TS-1 powder with binder solution and mixed for 30 minutes. Dough obtained after 30 minutes was transferred to an air oven and dried at 120° C. for 12 hours.

Post drying, the lumps obtained were pressed through a granulater of 1 mm dia (BSS 16 mesh) to make feed granules. This feed was then transferred to a tableting machine where in the feed was converted to tablets having both dia and length 3 mm These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 7.

Example 13

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Erich mixer for 15 minutes. To this mixture the binder solution was added slowly, while agitation was on in the Eirich mixer. Binder solution was mixed with TS-1 powder and HPMC in the Eirich mixer for 30 min. 100 g starch powder was added to the Eirich mixer containing TS-1 powder with binder solution and mixed for 30 minutes. Dough obtained after 30 minutes was transferred to an air oven and dried at 120° C. for 12 hours. Post drying, the lumps obtained were pressed through a granulater of 1 mm dia (BSS 16 mesh) to make feed granules. This feed was then transferred to a tableting machine where in the teed was converted to tablets having both dia and length 3 mm. These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 7.

TABLE 7

Properties of TS-1 based tablets/pellets with BD in the range of 0.62 to 0.69 kgs/lit. and CS in the range of 3.6 to 6.8 Kgs:

| Example No. | TS-1 Powder wt % in final catalyst (wt %) | Binder composition content (SiO2 wt %) | Ethyl silicate hydrolysis conditions | | | | | Ave. | |
|---|---|---|---|---|---|---|---|---|---|
| | | | DM water (ML) | Liq. Ammonia (ML) | HPMC (g) | Starch powder (g) | Stirring time (h) | drying time, (h) | Crushing strength (Kgs) | Bulk Density (Kg/lit) |
| 10 | 80 | 20 | 200 | 2 | 20 | 0 | 1 | 12 | 5.3 | 0.69 |
| 11 | 80 | 20 | 200 | 3 | 20 | 0 | 1 | 12 | 5 | 0.69 |

TABLE 7-continued

Properties of TS-1 based tablets/pellets with BD in the range of 0.62 to 0.69 kgs/lit. and CS in the range of 3.6 to 6.8 Kgs:

| Example No. | TS-1 Powder wt % in final catalyst (wt %) | Binder composition content (SiO2 wt %) | Ethyl silicate hydrolysis conditions | | | | | drying time, (h) | Ave. Crushing strength (Kgs) | Bulk Density (Kg/lit) |
|---|---|---|---|---|---|---|---|---|---|---|
| | | | DM water (ML) | Liq. Ammonia (ML) | HPMC (g) | Starch powder (g) | Stirring time (h) | | | |
| 12 | 80 | 20 | 200 | 2 | 20 | 100 | 1 | 12 | 6.8 | 0.62 |
| 13 | 80 | 20 | 200 | 2 | 20 | 100 | 1 | 12 | 3.6 | 0.62 |

Preparation of Pellets/Tablets with BD in the Range of 0.62 to 0.67 kgs/lit. and CS in the Range of 3.0 to 4.0 Kgs:

Example 13

As described above. The properties of the same are tabulated in the Table 8.

Example 14

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. 50 g starch powder was added to the Eirich mixer containing TS-1 powder with binder solution and mixed for 30 minutes. Dough obtained after 30 minutes was transferred to an air oven and dried at 120° C. for 12 hours. Post drying, the lumps obtained were pressed through a granulater of 1 mm dia (BSS 16 mesh) to make feed granules. This feed was then transferred to a tableting machine where in the feed was converted to tablets having both dia and length 3 mm. These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 8.

Preparation of Pellets/Tablets with BD Greater Than 0.65 kgs/lit. and CS Greater Than 5.0 Kgs:

Example 15

For making binder solution for 1 Kg TS-1 powder, 625 g ethyl silicate 40 was taken in a 2 liter poly propylene container. To this was added 200 ml DM water and 2 ml of 14 N liquor ammonia. This solution was stirred for 1 hr and then 100 g of starch powder was added to this solution. This solution was further mixed for 30 minutes. 1 Kg TS-1 powder was mixed with 20 g of HPMC in an Eirich mixer for 15 minutes. To this mixture the binder solution was added slowly, while agitation was on in the Eirich mixer. Binder solution was mixed with TS-1 powder and HPMC in the Eirich mixer for 30 min. Dough obtained after 30 minutes was transferred to an air oven and dried at 120° C. for 12 hours. Post drying, the lumps obtained were pressed through a granulater of 1 mm dia (BSS 16 mesh) to make feed granules. This feed was then transferred to a tableting machine where in the feed was converted to tablets having both dia and length 3 mm. These tablets were allowed to age for 12 hours at room temperature in an open atmosphere. Post ageing, the tablets were dried at 120° C. in an air oven for 12 hours, followed by calcinations in air flow at 550° C. for 3 hrs at a heating rate of 1.5° C./minute. Calcined TS-1 tablets constituted the shaped TS-1 product. The said product was characterized for crushing strength and bulk density. The properties of the same are tabulated in the Table 9.

TABLE 8

Properties of TS-1 based tablets/pellets with BD in the range of 0.62 to 0.67 kgs/lit. and CS in the range of 3.0 to 4.0 Kgs:

| Example No. | TS-1 Powder wt % in final catalyst (wt %) | Binder composition content (SiO2 wt %) | Ethyl silicate hydrolysis conditions | | | | | drying time, (h) | Ave. Crushing strength (Kgs) | Bulk Density (Kg/lit) |
|---|---|---|---|---|---|---|---|---|---|---|
| | | | DM water (ML) | Liq. Ammonia (ML) | HPMC (g) | Starch powder (g) | Stirring time (h) | | | |
| 13 | 80 | 20 | 200 | 2 | 20 | 100 | 1 | 12 | 3.6 | 0.62 |
| 14 | 80 | 20 | 200 | 2 | 20 | 50 | 1 | 12 | 3.6 | 0.67 |

TABLE 9

Properties of TS-1 based tablets/pellets with BD greater than 0.65 kgs/lit. and CS greater than 5.0 Kgs:

| Example No. | TS-1 Powder wt % in final catalyst (wt %) | Binder composition content (SiO2 wt %) | Ethyl silicate hydrolysis conditions | | | | | drying time, (h) | Ave. Crushing strength (Kgs) | Bulk Density (Kg/lit) |
|---|---|---|---|---|---|---|---|---|---|---|
| | | | DM water (ML) | Liq. Ammonia (ML) | HPMC (g) | Starch powder (g) | Stirring time (h) | | | |
| 15 | 80 | 20 | 200 | 2 | 20 | 100 | 1 | 12 | 6.8 | 0.68 |

Preparation of Pellets/Tablets with BD lesser than 0.65 kgs/lit.and CS Lesser Than 4.0 Kgs:

Example 13

As described above. The properties of the same are tabulated in the Table 10.

TABLE 10

Properties of TS-1 based tablets/pellets with BD lesser than 0.65 kgs/lit. and CS lesser than 4.0 Kgs.

| Example No. | TS-1 Powder wt % in final catalyst (wt %) | Binder composition content (SiO2 wt %) | Ethyl silicate hydrolysis conditions | | | | | drying time, (h) | Ave. Crushing strength (Kgs) | Bulk Density (Kg/lit) |
|---|---|---|---|---|---|---|---|---|---|---|
| | | | DM water (ML) | Liq. Ammonia (ML) | HPMC (g) | Starch powder (g) | Stirring time (h) | | | |
| 13 | 80 | 20 | 200 | 2 | 20 | 100 | 1 | 12 | 3.6 | 0.62 |

Within the scope of the invention, the binder may comprise a mixture of ETS-40 and other suitable binder materials. A number of suitable binder materials are known in the art and any of them can be in mixture with ETS-40, which is within the scope of the invention. Although the extrusions and tablets/pellets mentioned in the examples/tables can be formed with 3 mm diameter, the diameter can be varied from 1.5 mm to 4.5 mm which is within the scope of the invention. The length of the extrudates can be controlled by fitting a die cutter at the extruder outlet and controlling the length by rmp of die cutter, which is also within the scope of the invention. The length of tablets can be controlled by choosing the appropriate die/device during the tabeletting, which is also within the scope of the invention.

In summary, the advantages of the process of the invention over the prior art processes, are:

(i) Custom-making shaped TS-1 product with targeted physico-chemical attributes according to stipulations of various industrial processes employing Titanium catalysts;
(ii) the adoption of a novel binder composition;
(iii) a novel process engineering technique of the invention wherein superior control and optimization of the properties of the shaped TS-1 product is possible by means of novel steps in the process of the invention. Said properties over which control can be exercised are CS, BD, pore volume distribution and Ti availability/dispersibility of active sites. Said control being exercised by regulating the degree of hydrolysis of the ETS-40—ethanol-ammonia-water binder composition. In the novel method both the primary-hydrolysis, that is the degree of hydrolysis before the addition of the ETS-40 mixture to the TS-1 and the secondary-hydrolysis that occurs during the various processing operations in making the dried/calcined shaped TS-1 product are controlled;
(iv) the shaped TS-1 process of the invention can be worked with both calcined raw TS-1 powder or non-calcined powder, unlike the prior-art processes.
(v) the process step of spray drying in prior art processes being obviated by the unique process-recipe of this invention.
(vi) the process step of removing ethanol from the reaction mixture is also obviated.

We claim:

1. A method of making a shaped Titanium Silicalite-1 product, comprising the steps of:
   i) providing powdered raw Titanium Silicalite-1 material having undergone calcination;
   ii) adding to the Titanium Silicalite-1 material from step (i), a binder composition comprising a combination of one or more Oligomeric silicate and one or more alcohols, and at least one hydrolysing agent, the one or more alcohols generated as a result of hydrolysis of the one or more Oligomeric silicate;
   iii) forming the Titanium Silicalite-1 material mixture from step (ii) into a dough;
   iv) fabricating the dough from step (iii) into a shaped Titanium Silicalite-1 product;
   v) drying the shaped Titanium Silicalite-1 product from step (iv) at a temperature elevated from ambient temperature for a pre-determined period of time;
   wherein the properties of the shaped Titanium Silicalite-1 product are engineered by regulating one or more of the following, factors or suitable combinations thereof:
   (i) an amount of the at least one hydrolysing agent that is added;
   (ii) stage(s) of the reaction when the at least one hydrolysing agent is added;
   (iii) an amount of water along with the at least one hydrolysing agent;

(iv) an amount of the binder composition added;
(v) a duration of mixing of the binder composition and the at least one hydrolysing agent;
(vi) drying time and temperature.

2. The method of claim 1 wherein the binder composition comprises Ethyl silicate 40, ethanol, and liquor ammonia, and further wherein the ethanol generated during the reaction is retained and not distilled out prior to shaping the dough into extrudates/other shapes.

3. The method of claim 2 wherein for every 1 Kg of raw Titanium Silicalite-1 powder comprising 70 to 90 Wt % catalyst further comprising at least one of:
(a) adding Ethyl Silicate 40 comprising an SiO2 content of 5 to 50 Wt %;
(b) adding demineralized water in an amount of 80 to 400 ml;
(c) adding Ammonia being, 5 to 25 N and 1 to 6 ml;
(d) the pre-determined drying time in step (v) being 2 to 24 hours;
(e) the elevated temperature in the drying step (v) being 80 to 130 degree C.;
(f) calcining the Titanium Silicalite-1 for 2 to 12 hours;
(g) calcining the Titanium Silicalite-1 at a temperature of 400 to 600 deg. C;
(h) adding a blowing agent to further engineer or optimize Titanium Silicalite-1 combination attributes to match a given stipulation, being 1 to 20 wt %.

4. The method of claim 1 wherein, the said binder composition allows for turning out extrudates, tablets and pellets from both calcined as well as non-calcined raw TS-1 material.

5. The method of claim 1 wherein the properties of the shaped Titanium Silicalite-1 product can be engineered or optimized by employing one or more of the following steps, or any desirable combination thereof:
(i) a crushing strength and a bulk density can be gradually increased with increase in the binder composition content;
(ii) the crushing strength and the bulk density can be gradually decreased with increasing water content;
(iii) the crushing strength and the bulk density can be gradually decreased with increasing the content of the hydrolyzing agent;
(iv) the crushing strength and the bulk density can be gradually decreased with increasing stirring time during hydrolysis of the binder composition;
(v) the crushing strength and the bulk density can be gradually decreased with increasing drying time.

6. The method of claim 1 wherein physico-chemical properties of the end product are engineered or optimized by employing one or more of the following steps, or any desirable combination thereof:
(a) addition of a blowing agent to the binder composition alone or either with water or Ethyl silicate, to sustain a given value of crushing strength while varying a bulk density alone, which can be increased with decreasing a blowing agent content,
(b) addition of a blowing agent during mixing to make the dough not in combination with either Ethyl silicate or water, to drastically decrease a crushing strength alone,
(c) addition of the blowing agent along with ethyl silicate during the mixing to make the dough, to acutely increase the bulk density alone.

7. A process as claimed in claim 6 wherein the blowing agent is a carbohydrate.

8. A process as claimed in claim 1 wherein the availability of Titanium catalyst is increased by reducing the binder composition content.

9. A process as claimed in claim 1 wherein pore volume distribution is regulated by varying the hydrolysis time duration.

10. The method of claim 1 wherein the process employed to make shaped Titanium Silicalite-1 products obviates the need for spray-drying and remotion of alcohol generated during the process.

11. The method of claim 1, in which the Titanium silicate-1 product is a catalytic Titanium silicate-1 molecular sieve, and wherein physico-chemical attribute combinations of the Titanium silicate-1 product are defined by:
(1) the Titanium silicate-1 product is in the form of extrudates, wherein,
(a) bulk density is in the range of 0.58 to 0.62 kgs/lit. and crushing strength in the range of 4 to 7.5 Kgs; or
(b) bulk density is in the range of 0.57 to 0.65 kgs/lit. and crushing strength in the range of 3.5 to 4.5 Kgs; or
(c) bulk density is greater than 0.65 kgs/lit. and crushing strength greater than 7.5 Kgs; or
(d) bulk density is lesser than 0.58 kgs/lit. and crushing strength lesser than 3.5 Kgs; or
(e) Ti content is in the range of 1.4 wt % to 2.0 wt % with bulk density 0.54 to 0.67 kgs/lit and crushing strength 2.7 to 12.5 Kgs; or
(f) Micropore volume is 78 to 97%, Meso and macropore volume 22 to 3%, with bulk density 0.6 to 0.62 kgs/lit and crushing strength 7.2 to 6.3 Kgs; or
(2) the Titanium silicate-1 product is in the form of tablets or pellets, wherein,
(g) bulk density is in the range of 0.62 to 0.69 kgs/lit. and crushing strength in the range of 3.6 to 6.8 Kgs; or
(h) bulk density is in the range of 0.62 to 0.67 kgs/lit. and crushing strength in the range of 3.0 to 4.0 Kgs; or
(i) bulk density is greater than 0.65 kgs/lit. and crushing strength greater than 5.0 Kgs; or
(j) bulk density is lesser than 0.65 kgs/lit. and crushing strength lesser than 4.0 Kgs.

12. The method of claim 1, further comprising the step, after step (iv), of cutting, granulation, compacting or other fabrication operation.

13. The method of claim 1, wherein the dough from step (iii) is fabricated into a shaped Titanium Silicalite-1 product by extrusion, pelleting or tableting.

14. The method of claim 3, wherein the blowing agent includes starch.

15. The method of claim 3, wherein the SiO2 content is 10 to 30 Wt %.

16. The method of claim 3, wherein the demineralized water is in an amount of 160 to 320 ml.

17. The method of claim 3, wherein the Ammonia is 10 to 18 N and 1 to 3 ml.

18. The method of claim 3, wherein the pre-determined drying time in step (v) is 6 to 12 hours.

19. The method of claim 3, wherein the elevated temperature in the drying step (v) is 100-120 degree C.

20. The method of claim 3, wherein the Titanium Silicalite-1 is calcined for 4 to 6 hours.

21. The method of claim 3, wherein the Titanium Silicalite-1 is calcined at a temperature of 450 to 550 deg. C.

22. The method of claim 3, wherein the blowing agent ranges from 5 to 10 percent by weight.

* * * * *